(12) United States Patent
Mu et al.

(10) Patent No.: US 10,284,929 B2
(45) Date of Patent: May 7, 2019

(54) COMPUTER TOMOGRAPHY APPARATUS WITH A WIRELESS CONTROL SYSTEM

(71) Applicant: Siemens Healthcare GmbH, Erlangen (DE)

(72) Inventors: Hong De Mu, Shanghai (CN); Yin Jie Xiang, Shanghai (CN)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/499,249

(22) Filed: Apr. 27, 2017

(65) Prior Publication Data

US 2017/0318362 A1  Nov. 2, 2017

(30) Foreign Application Priority Data

Apr. 29, 2016 (CN) .................. 2016 1 0280677

(51) Int. Cl.
| | |
|---|---|
| *A61B 6/00* | (2006.01) |
| *H04Q 9/04* | (2006.01) |
| *H04W 76/11* | (2018.01) |
| *H04W 4/80* | (2018.01) |
| *A61B 6/03* | (2006.01) |
| *H04W 68/00* | (2009.01) |
| *H04W 80/00* | (2009.01) |
| *H04B 1/401* | (2015.01) |
| *H04W 12/06* | (2009.01) |

(52) U.S. Cl.
CPC ............ *H04Q 9/04* (2013.01); *A61B 6/032* (2013.01); *A61B 6/4494* (2013.01); *A61B 6/461* (2013.01); *A61B 6/467* (2013.01); *A61B 6/54* (2013.01); *A61B 6/548* (2013.01); *A61B 6/56* (2013.01); *H04W 4/80* (2018.02); *H04W 68/005* (2013.01); *H04W 76/11* (2018.02); *H04W 80/00* (2013.01); *H04B 1/401* (2013.01); *H04W 12/06* (2013.01)

(58) Field of Classification Search
None
See application file for complete search history.

(56) References Cited

U.S. PATENT DOCUMENTS

| | | | | |
|---|---|---|---|---|
| 6,968,242 B1 * | 11/2005 | Hwu | .................... | G05B 19/058 700/82 |
| 7,072,443 B2 | 7/2006 | Schick et al. | | |
| 2004/0067736 A1 * | 4/2004 | Kamma | ................ | H04W 12/06 455/41.2 |
| 2005/0088275 A1 * | 4/2005 | Valoteau | ................ | G08C 19/28 340/3.1 |
| 2005/0111420 A1 * | 5/2005 | Fujii | .................... | G06K 7/0008 370/338 |
| 2007/0080823 A1 * | 4/2007 | Fu | .......................... | G08C 23/04 340/4.3 |

(Continued)

*Primary Examiner* — Brian S Roberts
(74) *Attorney, Agent, or Firm* — Schiff Hardin LLP

(57) ABSTRACT

A computed tomography (CT) apparatus wireless controller has a CT main control circuit and a wireless main control circuit. The wireless main control circuit receives a control signal from a wireless secondary controller, and subjects the control signal to a validity check according to an identifier of the wireless secondary controller carried in the control signal when the control signal passes the check, it is supplied to the CT main control circuit from the wireless main control circuit. The CT main control circuit performs corresponding operation control according to the control signal.

11 Claims, 4 Drawing Sheets

| Device name | Device ID | Pairing state | | Activation state | |
|---|---|---|---|---|---|
| Wireless RMC1 | 1106135120160110 | Successfully paired | cancel pairing | activated | cancel activation |
| Wireless RMC2 | 1106135120160112 | Successfully paired | cancel pairing | not activated | activate |
| Wireless RMC3 | 1106135120160114 | not paired | pair | not activated | activate |

(56) References Cited

U.S. PATENT DOCUMENTS

2009/0036902 A1\* 2/2009 DiMaio ................. A61B 34/10
                                                606/130
2013/0272488 A1 10/2013 Bailey et al.

\* cited by examiner

COMPUTER TOMOGRAPHY APPARATUS WITH A WIRELESS CONTROL SYSTEM

BACKGROUND OF THE INVENTION

Field of the Invention

The present invention relates to the field of medical equipment, in particular a computed tomography (CT) wireless controller, a wireless control system, and a CT apparatus.

Description of the Prior Art

In certain medical devices, such as X-Ray computed tomography (CT) apparatuses, there will generally be at least one human apparatus interface (HMI) control component, to realize control of the operation of the medical device. At present, each HMI control component is directly connected to a motherboard of the medical device by a hardwired connection.

Thus, restricted by the length and topological structure of wired cables, HMI control components connected in a wired fashion may only be arranged in specific positions. For example, in CT apparatuses, it is generally necessary to perform control at different positions in response to different control demands.

When it is necessary to control X-rays to perform exposure imaging, the operator must generally perform exposure control in an operating room outside the imaging room, to prevent the operator from being subjected to unnecessary X-ray radiation; when it is necessary to control the X-ray source or patient table to perform complex movement, the operator must generally perform movement control beside the imaging device, to better observe whether movement positions are suitable, but if it is only necessary to control the X-ray source or patient table to perform simple movement, the operator may also perform movement control in the operating room. To fulfil different control demands, it is generally necessary to dispose multiple wired HMI control components at different positions. At present, these HMI control components may include control boxes, gantry control panels and foot-operated controllers, etc.

To better promote the rational deployment of resources, those skilled in the art are still making efforts to seek other ways of realizing HMI control components.

SUMMARY OF THE INVENTION

An object of the present invention is to provide a wireless controller, and a wireless control system, and a CT apparatus, for the purpose of facilitating the rational arrangement of control components.

A wireless main controller proposed in accordance with the present invention has a CT main control circuit and a wireless main control circuit. The wireless main control circuit receives a control signal from a wireless secondary controller, and subjects the control signal to a validity check according to an identifier of the wireless secondary controller carried in the control signal. A control signal that has passed the check is supplied by the wireless main control circuit to the CT main control circuit that, upon receiving the control signal from the wireless main control circuit performs corresponding control according to the control signal.

An embodiment includes a human-apparatus interface that receives a pairing request signal, and supplies the pairing request signal to the CT main control circuit. The pairing request signal includes an identifier of the wireless secondary controller. The CT main control board supplies the pairing request signal to the wireless main control board after receiving the pairing request signal, and receives pairing result information fed back by the wireless main control board, and presents the pairing result information via the human-apparatus interface. The wireless main control board is further designed to send a pairing instruction to the corresponding wireless secondary controller according to the identifier in the pairing request signal, and to enter into a pairing mode state, in which it waits to receive a pairing confirmation signal from the wireless secondary controller. If a pairing confirmation signal from the wireless secondary controller is correctly received, the wireless main control signal determines that pairing with the wireless secondary controller is successful, and otherwise determines that pairing with the wireless secondary controller has failed, and feeds back pairing result information to the CT main control board. Upon determining that pairing with the wireless secondary controller is successful, the wireless main control circuit sends pairing result information indicating pairing success to the corresponding wireless secondary controller. After receiving a control signal from the wireless secondary controller, the wireless main control board confirms that the control signal is a valid control signal if it is determined, on the basis of the identifier of the wireless secondary controller carried in the control signal, that the wireless secondary controller has been successfully paired.

In another embodiment, the CT main control board, after receiving the pairing request signal, is designed to present input prompt information for a pairing sequence code via the human-apparatus interface and/or an external display screen; as well as to carry the pairing sequence code in the pairing request signal and supply this to the wireless main control board. When received pairing result information fed back by the wireless main control board indicates successful pairing, the CT main control circuit controls the human-apparatus interface and/or the external display screen to stop displaying the input prompt information for the pairing sequence code. The pairing confirmation signal includes a pairing check code corresponding to the pairing sequence code prompt information. The wireless main control board, after receiving the pairing confirmation signal from the wireless secondary controller, compares the pairing check code in the pairing confirmation signal with the pairing sequence code carried in the pairing request signal, and when the two are the same, determines that the pairing confirmation signal from the wireless secondary controller has been correctly received.

In another embodiment, the CT main control board, after receiving the pairing request signal, is designed to carry a pairing sequence code in the pairing request signal, and supply the pairing request signal carrying the pairing sequence code to the wireless main control board. The wireless main control board is designed to carry the pairing sequence code in the pairing instruction and sending this to the corresponding wireless secondary controller. After receiving a pairing confirmation signal that includes a pairing check code from the wireless secondary controller, the wireless main control circuit is designed to compare the pairing check code in the pairing confirmation signal with the pairing sequence code carried in the pairing request signal, and if the two are the same, to determine that the pairing confirmation signal from the wireless secondary controller has been correctly received.

In another embodiment, the human-apparatus interface is designed to receive an activation request signal for a successfully paired wireless secondary controller, and to supply the activation request signal to the CT main control board. The activation request signal includes an identifier of the wireless secondary controller. The CT main control board is designed to supply the activation request signal to the wireless main control board after receiving the activation request signal and, upon receiving activation result information fed back by the wireless main control board, and to present the activation result information by via the human-apparatus interface. After receiving a control signal from a wireless secondary controller, the wireless main control board is further designed to confirm that the control signal is a valid control signal if it is determined, on the basis of the identifier of the wireless secondary controller carried in the control signal, that the wireless secondary controller has been paired successfully and activated.

A wireless secondary controller in accordance with the present invention has a human-apparatus interface and a wireless transceiving processor. The human-apparatus interface and the wireless transceiving processor are connected via serial peripheral interface pins and/or input/output pins. The human-apparatus interface is designed to receive a control signal, and to supply the control signal to the wireless transceiving processor. The wireless transceiving processor is designed to carry an identifier of the wireless secondary controller in the control signal, and to transmit the control signal carrying the identifier.

In an embodiment, the human-apparatus interface module is further designed to receive a pairing confirmation signal before receiving the control signal, and to supply the pairing confirmation signal to the wireless transceiving processor. The wireless transceiving processor is further designed to receive a pairing instruction from the wireless main controller, and to enter into a pairing mode state, and to receive the pairing confirmation signal from the human-apparatus interface module, and to transmit the pairing confirmation signal, and to enter into an operating mode state if a pairing success message from the wireless main controller is received.

In an embodiment, the pairing confirmation signal includes a pairing check code.

In another embodiment, the wireless transceiving processor is further used for supplying the pairing instruction to the human-apparatus interface, and a display unit of the human-apparatus interface presents the pairing sequence code carried in the pairing instruction.

In an embodiment, the human-apparatus interface has multiple control buttons and each control button has an associated, first interface circuit, second interface circuit and an analog-to-digital converter. Each control button has two independent switch contacts, with one switch contact connected to an input/output interface pin of the wireless transceiving processor via a first interface circuit, and the other switch contact connected to a serial peripheral interface pin of the wireless transceiving processor via a second interface circuit and an analog-to-digital converter. The wireless transceiving processor, before carrying the identifier of the wireless secondary controller in the control signal, compares a control signal received via the input/output interface pin with a control signal received via the serial peripheral interface pin, and if the two are the same, carries the identifier of the wireless secondary controller in the control signal.

A wireless control system in accordance with the present invention has wireless main controller as described above and the wireless secondary controller as described above.

A CT apparatus in accordance with the present invention has the abovementioned wireless control system, or the wireless main controller described above. The CT apparatus in accordance with the present invention, except for the inventive wireless control system or wireless main controller described above, includes the conventional components, in a conventional structure, that are present in commercially available CT apparatuses. These components include, at a minimum, a stationary frame with a rotor having a central opening therein, the rotor being mounted to rotate in the stationary frame around a center axis that proceeds through the opening. An x-ray source and a radiation detector are mounted on the rotor. CT data are acquired thereby and are provided to a processor for reconstruction of an image therefrom in a known manner.

Since the CT apparatus in accordance with the present invention has a wireless control system having a wireless main controller and at least one wireless secondary controller, the wireless main controller receives and identifies a control message from a corresponding wireless secondary controller through a wireless channel, and can realize corresponding operation control, such that the wireless secondary controllers serving as CT apparatus control components can be arranged as required, and no longer be subject to the restrictions of hardwired connections.

In addition, by performing a paired connection with corresponding wireless secondary controllers one by one, the reliability of data communication with corresponding wireless secondary controllers can be ensured.

Moreover, through the use of verification by comparison of a pairing sequence code and a pairing check code, the reliability of data communication with corresponding wireless secondary controllers can be further ensured.

In addition, by controlling a paired wireless secondary controller to enter an activation state, the operational safety of the CT apparatus can be further ensured.

Furthermore, the provision of independent switch contacts on a control button side of the wireless secondary controller enables the same control signal to be independently sent to a wireless transceiving processor of the wireless secondary controller via channels corresponding to different switch points, so that a single fault of the button can be avoided, thereby further ensuring the operational safety of the CT apparatus.

DESCRIPTION OF THE PREFERRED EMBODIMENTS

In order to explain the object, technical solution and advantages of the present invention, the present invention is described in detail below via a number embodiments.

Figure 1:
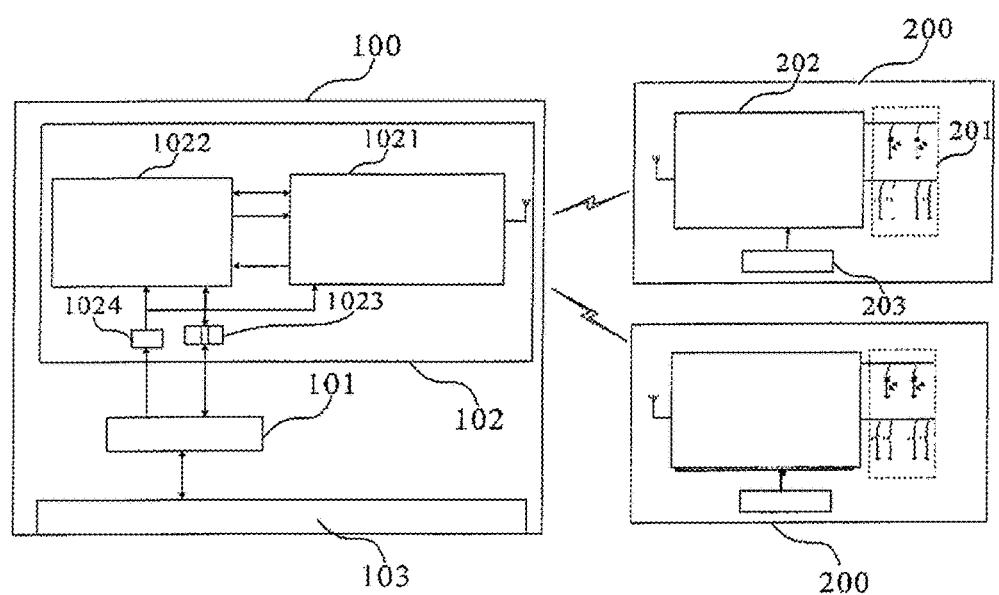
FIG. 1 is a block diagram of a wireless control system in an embodiment of the present invention.

FIG. 1 is a block diagram of a wireless control system in an embodiment of the present invention. As FIG. 1 shows, the wireless control system includes a wireless main controller 100 and at least one wireless secondary controller 200.

Each wireless secondary controller 200 is designed to receive a control signal. An identifier of the wireless secondary controller 200 is carried in the control signal. Each secondary controller 200 transmits the control signal carrying the identifier. Each wireless secondary controller has one unique identifier (ID) number.

When more than one wireless secondary controller 200 is present, the wireless secondary controllers 200 can execute exactly the same functions, or partly the same functions, or completely different functions. For example, a manually-controlled wireless secondary controller 200 and a foot-operated wireless secondary controller 200 may be used. Alternatively, two manually-controlled wireless secondary controllers 200 may be used. Alternatively, two manually-controlled wireless secondary controllers 200 and a foot-operated wireless secondary controller 200 etc. may be used.

The wireless main controller 100 is designed to receive the control signal from the wireless secondary controller 200, and to subject the control signal to a validity check according to the identifier of the wireless secondary controller 200 carried in the control signal. If the check is passed, the main controller 100 performs operational control of the CT apparatus according to the control signal.

Furthermore, in embodiments wherein there is more than one wireless secondary controller 200, in order to better receive control signals from each secondary controller 200, the wireless secondary controllers 200 may be paired in advance.

In such embodiments, the wireless main controller 100 receives a pairing request signal of a user for a wireless secondary controller 200, the pairing request signal including an identifier of the wireless secondary controller 200. On the basis of the identifier in the pairing request signal, the corresponding wireless secondary controller 200 sends a pairing instruction, and enters a pairing mode state. If it is determined that the pairing confirmation signal from the wireless secondary controller 200 is received correctly, then it is determined that pairing with the wireless secondary controller 200 is successful. Otherwise, it is determined that pairing with the wireless secondary controller 200 has failed, and information about the result of pairing with the wireless secondary controller 200 is presented to the user. Moreover, when pairing is successful, a pairing success message is sent to a wireless secondary controller 200.

A wireless secondary controller 200 receives the pairing instruction, enters a pairing mode state, waits to receive a pairing confirmation signal entered by a user, and sends the pairing confirmation signal to the wireless main controller 100. If a pairing success message is received from the wireless main controller 100, then an operating mode state is entered.

In an embodiment of the present invention, the pairing confirmation signal may be a pairing confirmation signal entered by a user by clicking on a confirmation button, or may be a pairing confirmation signal entered by a user according to a specific indication of the pairing instruction, or may be a pairing confirmation signal entered by a user according to a specific indication of the wireless main controller 100.

When pairing is performed, the wireless main controller 100 may generate a pairing sequence code, e.g. a random sequence code, or may set at least one pairing sequence code in advance, and selects different pairing sequence codes for different communication or different wireless secondary controllers 200, or may universally employ one identical pairing sequence code, etc. and intimate the pairing sequence code to a user of a corresponding wireless secondary controller 200, so that the user enters a pairing check code corresponding to the pairing sequence code, and then the wireless secondary controller 200 can carry the pairing check code in pairing confirmation information and send this to the wireless main controller 100. The wireless main controller 100, after receiving the pairing confirmation signal, compares the pairing check code in the pairing confirmation signal with the pairing sequence code, and if the two are the same, determines that the pairing confirmation signal from the wireless secondary controller 200 has been correctly received.

A prompt can be made to a user of a corresponding wireless secondary controller 200, via a display of the wireless secondary controller 200 or via an external display screen, the wireless main controller 100 in order to remind the user to enter the pairing sequence code on the corresponding wireless secondary controller 200, so as to generate a corresponding pairing check code. The external display screen may be a display screen on the CT gantry (GDP, Gantry Display Panel). Alternatively, the wireless main controller 100 may carry the pairing sequence code in a pairing instruction and send this to a corresponding wireless secondary controller 200, and the pairing sequence code is presented by a display unit of the wireless secondary controller 200.

For example, prompt information is: "Would the user please press the sequence of button 1, button 2 and button 3 in order within 30 s and click on the wireless secondary controller (setup ID: 1106135120160112)".

The wireless main controller 100 may furthermore receive a cancel pairing request signal entered by a user for a successfully paired wireless secondary controller 200, and then cancel receipt of a control message from the corresponding wireless secondary controller 200 according to an identifier of the wireless secondary controller 200 carried in the cancel pairing request signal. The wireless controller 100 then filters a message from the wireless secondary controller 200, and presents cancel pairing result information.

In addition, in an embodiment of the present invention, to further ensure operation safety, an activation state may also be set for successfully paired wireless secondary controllers 200.

Correspondingly, the wireless main controller 100 may furthermore receive an activation request signal entered by a user for a successfully paired wireless secondary controller 200, and then wait to receive a control message from the corresponding wireless secondary controller 200 according to an identifier of a wireless secondary controller 200 carried in the activation request signal, and filter a message from another wireless secondary controller 200. The wireless main controller 100 then presents activation result information.

After receiving a control signal from a wireless secondary controller 200, the wireless main controller 100 can determine, according to an identifier of the wireless secondary controller 200 carried in the control signal, whether the wireless secondary controller 200 has been paired successfully and activated, and if it has been, confirm that the control signal is a valid control signal.

Figures 2, 3:
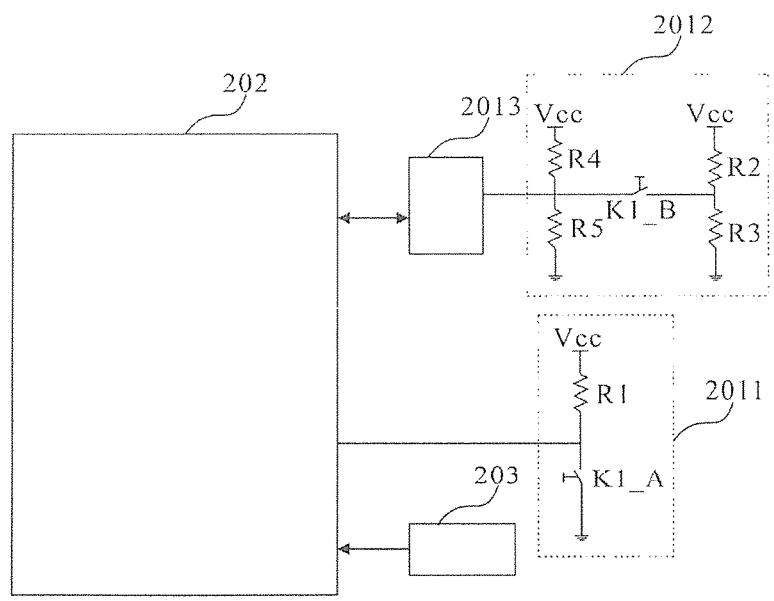
FIG. 2 is a presentation interface for information about results such as pairing and activation of the wireless secondary controllers in one example of the present invention.
FIG. 3 is a block diagram of a dual-contact control button of the human-apparatus interface module in one example of the present invention.

FIG. 2 shows a presentation interface for information about results such as pairing and activation of the wireless secondary controllers in one example. The device Wireless RMC1 has been paired successfully and activated; the device Wireless RMC2 has been successfully paired but not activated; the device Wireless RMC3 has not been paired and not been activated.

In addition, the wireless main controller 100 may furthermore receive a deactivation request signal entered by a user for an activated wireless secondary controller 200, cancel receipt of a control message from the corresponding wireless secondary controller 200 according to an identifier of a wireless secondary controller 200 carried in the deactivation request signal, and filter a message from the wireless secondary controller 200; and moreover present deactivation result information.

In an embodiment of the present invention, in the case where a wireless secondary controller 200 has a control button, the wireless secondary controller 200 may receive a first sub-signal and a second sub-signal corresponding to a control signal by means of a control button having dual switch contacts, in order to prevent a single fault of the control button of the wireless secondary controller 200. The first sub-signal may be a first digital control signal entered via one switch contact of the control button, and the second sub-signal may be a second digital control signal obtained by conversion via an analog-to-digital converter of an analog control signal entered via the other switch contact of the control button. Thereafter, the wireless secondary controller 200 may compare the first sub-signal and second sub-signal, and if the two are the same, carry an identifier of the wireless secondary controller 200 in the control signal and send this to the wireless main controller 100.

In embodiments of the present invention, the wireless main controller 100 may have multiple specific implementations of internal structure. FIG. 1 shows just one of these. As FIG. 1 shows, the wireless main controller 100 includes a CT main control circuit 101, a wireless main control circuit 102 and a human-apparatus interface 103.

The wireless main control circuit 102 is designed to receive a control signal from a wireless secondary controller 200, subjecting the control signal to a validity check according to an identifier of the wireless secondary controller 200 carried in the control signal, and supplying the control signal that has passed the check to the CT main control circuit 101.

The CT main control circuit 101 is designed to receive a control signal from the wireless main control circuit 102, and to perform corresponding operation control according to the control signal.

If it is necessary to perform pairing with a wireless secondary controller 200 before performing formal control communication, the human-apparatus interface 103 is designed to receive a pairing request signal, and to supply the pairing request signal to the CT main control circuit 101. The pairing request signal includes an identifier of a wireless secondary controller 200. Correspondingly, after receiving the pairing request signal, the CT main control circuit 101 supplies the pairing request signal to the wireless main control circuit 102; and receives pairing result information fed back by the wireless main control circuit 102, and presents the pairing result information via the human-apparatus interface 103. On the basis of the identifier in the pairing request signal, the wireless main control circuit 102 sends a pairing instruction to the corresponding wireless secondary controller 200, and enters a pairing mode state, wherein it waits to receive a pairing confirmation signal from the wireless secondary controller 200. If a pairing confirmation signal from the wireless secondary controller 200 is correctly received, the wireless main control circuit 102 determines that pairing with the wireless secondary controller 200 is successful, and otherwise determines that pairing with the wireless secondary controller 200 has failed, and feeds back pairing result information to the CT main control circuit 101. Upon determining that pairing with the wireless secondary controller 200 is successful, the wireless main control circuit 102 sends pairing result information indicating pairing success to the corresponding wireless secondary controller 200.

After receiving a control signal from a wireless secondary controller 200, the wireless main control circuit 102 confirms that the control signal is a valid control signal if it is determined, on the basis of an identifier of the wireless secondary controller 200 carried in the control signal, that the wireless secondary controller has been successfully paired.

In one embodiment, after receiving the pairing request signal, the CT main control circuit 101 may furthermore present input prompt information for a pairing sequence code via the human-apparatus interface 103 and/or an external display screen, and carries the pairing sequence code in the pairing request signal and supplies this to the wireless main control circuit 102. When the received pairing result information fed back by the wireless main control circuit 102 indicates successful pairing, the main control circuit 101 controls the human-apparatus interface 103 and/or the external display screen to stop displaying the input prompt information for the pairing sequence code.

Correspondingly, the pairing confirmation signal from the wireless secondary controller 200 includes a pairing check code entered by a user according to the pairing sequence code prompt information.

After receiving the pairing confirmation signal from the wireless secondary controller 200, the wireless main controller 102 compares the pairing check code in the pairing confirmation signal with the pairing sequence code carried in the pairing request signal, and if the two are the same, determines that the pairing confirmation signal from the wireless secondary controller 200 has been correctly received.

In another embodiment, after the CT main control circuit 101 supplies the pairing request signal carrying the pairing sequence code to the wireless main control circuit 102. The wireless main control circuit 102 may furthermore carry the pairing sequence code in the pairing instruction and send this to the corresponding wireless secondary controller 200; and after receiving a pairing confirmation signal that includes a pairing check code from the wireless secondary controller 200, the corresponding wireless secondary controller 200 compares the pairing check code in the pairing confirmation signal with the pairing sequence code carried in the pairing request signal, and if the two are the same, determines that the pairing confirmation signal from the wireless secondary controller 200 has been correctly received.

In addition, the human-apparatus interface 103 may furthermore receive a cancel pairing request signal entered by a user for a successfully paired wireless secondary controller 200, and supply the cancel pairing request signal to the CT main control circuit 101. The cancel pairing request signal includes an identifier of a wireless secondary controller 200. Correspondingly, after receiving the cancel pairing request signal, the CT main control circuit 101 supplies the cancel pairing request signal to the wireless main control circuit 102, and receives cancel pairing result information fed back by the wireless main control circuit 102, and presents the cancel pairing result information via the human-apparatus interface 103. The wireless main control circuit 102, on the basis of an identifier in the cancel pairing request signal, cancels receipt of a control message from the corresponding wireless secondary controller 200, and filters a message from the wireless secondary controller 200.

In another embodiment, the human-apparatus interface 103 may furthermore receive an activation request signal entered by a user for a successfully paired wireless secondary controller, and supply the activation request signal to the CT main control circuit 101. The activation request signal includes an identifier of a wireless secondary controller 200.

After receiving the activation request signal, the CT main control circuit 101 may furthermore supply the activation request signal to the wireless main control circuit 102, and receives activation result information fed back by the wireless main control circuit 102, and presents the activation result information by means of the human-apparatus interface 103.

On the basis of the identifier in the activation request signal, the wireless main control circuit 102 furthermore waits to receive a control message from the corresponding wireless secondary controller 200, and filters a message from another wireless secondary controller, and after receiving a control signal from a wireless secondary controller 200, confirms that the control signal is a valid control signal if it is determined, on the basis of an identifier of the wireless secondary controller 200 carried in the control signal, that the wireless secondary controller 200 has been paired successfully and activated.

In addition, the human-apparatus interface 103 may furthermore receive a deactivation request signal entered by a user for an activated wireless secondary controller 200, and supply the deactivation request signal to the CT main control circuit 101. The deactivation request signal includes an identifier of a wireless secondary controller 200. Correspondingly, after receiving the deactivation request signal, the CT main control circuit 101 supplies the deactivation request signal to the wireless main control circuit 102, and receives deactivation result information fed back by the wireless main control circuit 102, and presents the deactivation result information via the human-apparatus interface 103. The wireless main control circuit 102, on the basis of an identifier in the deactivation request signal, cancels receipt of a control message from the corresponding wireless secondary controller 200, and filters a message from the wireless secondary controller 200.

The internal structure of the wireless main control circuit 102 may have multiple specific implementations. FIG. 1 shows just one of these. As FIG. 1 shows, the wireless main control circuit 102 may include a wireless transceiving processor 1021, a microprocessor 1022, a physical layer interface 1023 and a power supply adaptor 1024.

The wireless transceiving processor 1021 and the microprocessor 1022 are connected via corresponding serial peripheral interface (SPI) pins and input/output (I/O) pins. The microprocessor 1022 is electrically connected to the CT main control circuit 101 via the physical layer interface 1023; the microprocessor 1022 and a power supply interface of the wireless transceiving processor 1021 are each connected to a power supply line of the CT main control circuit 101 via the power supply adaptor 1024.

The wireless transceiving processor 1021 is mainly used to accomplish data processing of a wireless transmission protocol; the microprocessor 1022 is mainly used to accomplish data conversion between the wireless transceiving processor 1021 and CT main control circuit 101. In addition, the check processing of the control signal is mainly accomplished by the microprocessor 1022.

In embodiments of the present invention, the internal structure of the wireless secondary controller 200 may also have multiple specific implementations. FIG. 1 shows just one of these. As FIG. 1 shows, the wireless secondary controller 200 may include a human-apparatus interface 201, a wireless transceiving processor 202, and a power supply 203.

The human-apparatus interface module 201 and wireless transceiving processor 202 are correspondingly connected via SPI pins and/or I/O pins.

The human-apparatus interface 201 is designed to receive a control signal, and to supply the control signal to the wireless transceiving processor 202.

The wireless transceiving processor 202 is designed to carry an identifier of the wireless secondary controller 200 in the control signal, and to send the control signal carrying the identifier to the wireless main controller 100.

The power supply module 203 is designed to supply power to the human-apparatus interface 201 and the wireless transceiving processor 202 from a battery.

Corresponding to the function of the wireless main controller 100, in one embodiment, the human-apparatus interface 201 may furthermore receive a pairing confirmation signal entered by a user before receiving the control signal, and supply the pairing confirmation signal to the wireless transceiving processor 202.

The wireless transceiving processor 202 is furthermore designed to receive a pairing instruction from the wireless main controller 100, and to enter a pairing mode state, waiting to receive a pairing confirmation signal from the human-apparatus interface module 201. After receiving the pairing confirmation signal, the wireless transceiving processor 202 sends the pairing confirmation signal to the wireless main controller 100; and if a pairing success message is received from the wireless main controller 100, enters into an operating mode state.

Corresponding to the function of the wireless main controller 100, if the wireless main controller 100 presents input prompt information for a pairing sequence code via its own human-apparatus interface 103 or an external display screen, then the pairing confirmation signal received by the human-apparatus interface 201 may include a pairing check code entered by a user according to the input prompt information for the pairing sequence code.

If the wireless main controller 100 carries a pairing sequence code in a pairing instruction and sends this to a wireless secondary controller 200, then the wireless transceiving processor 202 of the wireless secondary controller 200 may furthermore supply the pairing instruction to the human-apparatus interface 201, and a display unit of the human-apparatus interface 201 presents the pairing sequence code carried in the pairing instruction. Then the pairing confirmation signal received by the human-apparatus interface 201 may include a pairing check code entered by a user according to the pairing sequence code.

In one embodiment, when the human-apparatus interface 201 uses a control button as a signal input, each control button may be a control button having dual switch contacts, in order to prevent a single fault of the control button, so that a first sub-signal and a second sub-signal corresponding to the same signal can be respectively received via pathways in which the two contacts of the control button are located. The first sub-signal may be a first digital signal entered via one switch contact of the control button, and the second sub-signal may be a second digital signal obtained by conversion via an analog-to-digital converter of an analog control signal entered via the other switch contact of the control button.

Thereafter, the wireless transceiving processor 202 compares the first sub-signal and second sub-signal, and if the two are the same, carries an identifier of the wireless secondary controller 200 in the signal and send this to the wireless main controller 100.

For clarity, using one of the control buttons as an example, FIG. 3 shows a schematic diagram of a dual-contact control button of the human-apparatus interface 201 in one example of the present invention. As FIG. 3 shows, the human-apparatus interface 201 may include multiple control buttons K1 (only one control button is shown in FIG. 3), and, corresponding to each control button K1, a first interface circuit 2011, a second interface circuit 2012 and an analog-to-digital converter 2013.

Each control button K1 has two independent switch contacts K1_A, K1_B, wherein one switch contact K1_A is connected to an I/O interface pin of the wireless transceiving processor 202 via the first interface circuit 2011, and the other switch contact K1_B is connected to an SPI pin of the wireless transceiving processor 202 via the second interface circuit 2012 and the analog-to-digital converter 2013.

The first interface circuit 2011 has a first resistor R1 which has one end connected to a HIGH level and another end connected to one end of the switch contact K1_A, the other end of the switch contact K1_A being connected to ground. A non-grounded end of the switch contact K1_A is connected to an I/O interface pin of the wireless transceiving processor 202.

The second interface circuit 2012 has a second resistor R2, a third resistor R3, a fourth resistor R4 and a fifth resistor R5. The second resistor R2 has one end connected to a HIGH level and another end connected to one end of the switch contact K1_B and one end of the third resistor R3; the other end of the third resistor R3 is connected to ground; the fourth resistor R4 has one end connected to a HIGH level and another end connected to the other end of the switch contact K1_B and one end of the fifth resistor R5; the other end of the fifth resistor R5 is connected to ground; that end of the switch contact K1_B which is connected to the fourth resistor R4 is connected to an SPI pin of the wireless transceiving processor 202.

Once the control button K1 has been pressed, the switch contact K1_A is closed, and the wireless transceiving processor 202 receives a LOW signal; when the switch contact K1_A is opened, the wireless transceiving processor 202 receives a HIGH signal from the first interface circuit 2011.

Once the control button K1 has been pressed, the switch contact K1_B is closed, and the analog-to-digital converter 2013 acquires a first analog signal value from the second interface circuit 2012; when the switch contact K1_B is closed, the analog-to-digital converter 2013 acquires a second analog signal value from the second interface circuit 2012. The analog-to-digital converter 2013 converts the analog signal acquired to a digital signal and then supplies this to the wireless transceiving processor 202; the wireless transceiving processor 202 can determine whether K1_B is open or closed by means of the value read.

The processor only deems the state of the button to be valid when the states of K1_A and K1_B read by the wireless transceiving processor 202 are the same; otherwise, the processor deems the state of the button to be invalid.

The entry of the wireless main controller 100 into a pairing mode state, as mentioned in an embodiment of the present invention, may involve the wireless main controller 100 starting a pairing timer. The range of values which may be chosen for the pairing timer may be 30-120 seconds, etc., e.g. a value of 30 seconds, 1 minute, 1.5 minutes or 2 minutes etc. may be chosen. If no pairing confirmation signal sent from a wireless secondary controller 200 has been received within the time limit, then it can be determined that the current pairing has failed.

The entry of the wireless secondary controller 200 into a pairing mode state, as mentioned in an embodiment of the present invention, may involve the wireless secondary controller 200 starting a pairing timer. The range of values which may be chosen for the pairing timer may also be 30-120 seconds, etc., e.g. a value of 30 seconds, 1 minute, 1.5 minutes or 2 minutes etc. may be chosen. If no pairing confirmation signal entered by a user has been received within the time limit, then it can be determined that the current pairing has failed.

The CT apparatus in an embodiment of the present invention has a wireless control system implemented in any one of the abovementioned forms; or a wireless main controller implemented in any one of the abovementioned forms.

The wireless control system in embodiments of the present invention has been described in detail above; the wireless control method in embodiments of the present invention is described in detail below. The wireless control method in embodiments of the present invention may be applied to the wireless control system described above. For details which are not disclosed in the wireless control method of this embodiment, reference may be made to the description of corresponding parts in the wireless control system in the embodiments above.

Figure 4:
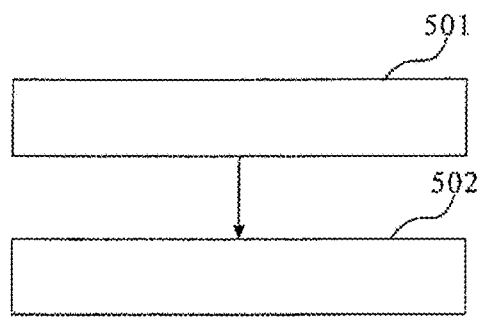
FIG. 4 is a flowchart of a wireless control method in an embodiment of the present invention.

FIG. 4 is an exemplary flowchart of a wireless control method in an embodiment of the present invention. The wireless control method may be applied in a wireless control system comprising a wireless main controller and at least one wireless secondary controller. As FIG. 4 shows, the method may comprise the following steps:

Step 501, a wireless secondary controller receives a control signal, carries an identifier of the wireless secondary controller in the control signal, and sends the control signal carrying the identifier to a wireless main controller; the wireless secondary controller is one of the at least one wireless secondary controllers.

In this step, the wireless secondary controller may receive a first sub-signal and a second sub-signal corresponding to the control signal by means of a control button having dual switch contacts; the first sub-signal is a first digital control signal entered via one switch contact of the control button, and the second sub-signal is a second digital control signal obtained by conversion via an analog-to-digital converter of an analog control signal entered via the other switch contact of the control button; the wireless secondary controller compares the first sub-signal and second sub-signal, and if the two are the same, carries an identifier of the wireless secondary controller in the control signal.

Step 502, the wireless main controller receives a control signal from the wireless secondary controller, subjects the control signal to a validity check according to the identifier of the wireless secondary controller carried in the control signal, and if the check is passed, performs corresponding operation control according to the control signal.

Figure 5:
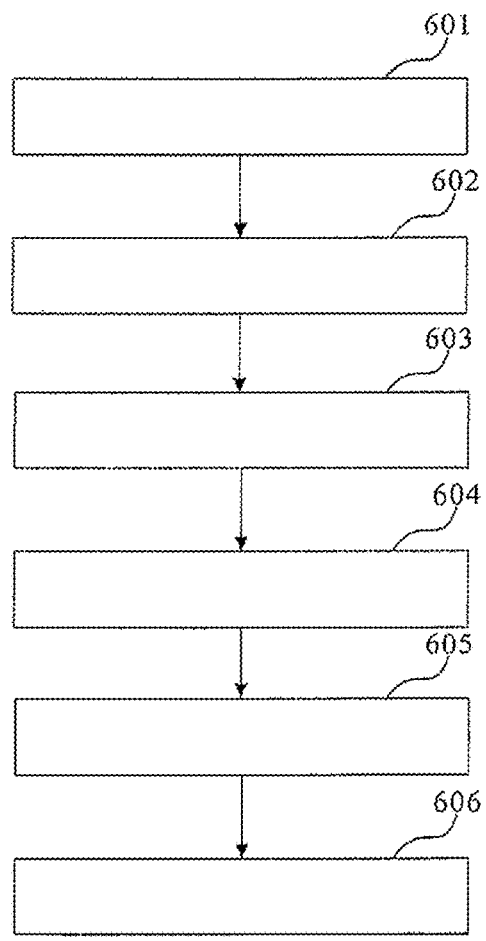
FIG. 5 is a demonstrative flowchart of wireless control method in another embodiment of the present invention.

FIG. 5 is an exemplary flowchart of another wireless control method in an embodiment of the present invention. The wireless control method may be applied in a wireless control system comprising a wireless main controller and at least one wireless secondary controller. As FIG. 5 shows, the method may comprise the following steps:

Step 601, a wireless main controller receives a pairing request signal entered by a user, the pairing request signal comprising an identifier of a wireless secondary controller; sends a pairing instruction to the corresponding wireless secondary controller according to the identifier in the pairing request signal, and enters a pairing mode state.

In this step, the wireless main controller may present a pairing sequence code by means of the wireless main controller or an external display screen; or the wireless main controller carries a pairing sequence code in a pairing instruction and sends this to the wireless secondary controller.

Step 602, the wireless secondary controller receives the pairing instruction, enters a pairing mode state, receives a pairing confirmation signal entered by a user, and sends the pairing confirmation signal to the wireless main controller.

In this step, in the case where the pairing sequence code is presented by means of the wireless main controller or an external display screen, the user, when entering the pairing confirmation signal, may enter a pairing check code corresponding to the pairing sequence code according to the information presented. In the case where the wireless main controller carries a pairing sequence code in a pairing instruction and sends this to the wireless secondary controller, the wireless secondary controller may present the pairing sequence code via its own display unit, so that the user, when entering the pairing confirmation signal, may enter a pairing check code corresponding to the pairing sequence code according to the information presented.

Step 603, the wireless main controller, if it determines that a pairing confirmation signal from the wireless secondary controller is correctly received, determines that pairing with the wireless secondary controller is successful; otherwise, it determines that pairing with the wireless secondary controller has failed, and presents information about the result of pairing with the wireless secondary controller; and when pairing is successful, sends a pairing success message to the wireless secondary controller.

In this step, in the case where there is a pairing sequence code, the wireless main controller, after receiving the pairing confirmation signal from the wireless secondary controller, may compare the pairing check code in the pairing confirmation signal with the pairing sequence code, and when the two are the same, determine that the pairing confirmation signal from the wireless secondary controller has been correctly received.

Step 604, the wireless secondary controller, if it receives a pairing success message from the wireless main controller, enters an operating mode state.

Step 605, a wireless secondary controller receives a control signal, carries an identifier of the wireless secondary controller in the control signal, and sends the control signal carrying the identifier to a wireless main controller; the wireless secondary controller is one of the at least one wireless secondary controllers.

In this step, the wireless secondary controller may receive a first sub-signal and a second sub-signal corresponding to the control signal by means of a control button having dual switch contacts; the first sub-signal is a first digital control signal entered via one switch contact of the control button, and the second sub-signal is a second digital control signal obtained by conversion via an analog-to-digital converter of an analog control signal entered via the other switch contact of the control button; the wireless secondary controller compares the first sub-signal and second sub-signal, and if the two are the same, carries an identifier of the wireless secondary controller in the control signal.

Step 606, the wireless main controller receives a control signal from the wireless secondary controller, and determines whether the wireless secondary controller has been paired successfully according to the identifier of the wireless secondary controller carried in the control signal, and if it has been, confirms that the control signal is a valid control signal, and performs corresponding operation control according to the control signal.

In addition, the wireless main controller may furthermore receive a cancel pairing request signal entered by a user for a successfully paired wireless secondary controller, cancel receipt of a control message from the corresponding wireless secondary controller according to an identifier of the wireless secondary controller carried in the cancel pairing request signal, and filter a message from the wireless secondary controller; and moreover present cancel pairing result information.

Figure 6:
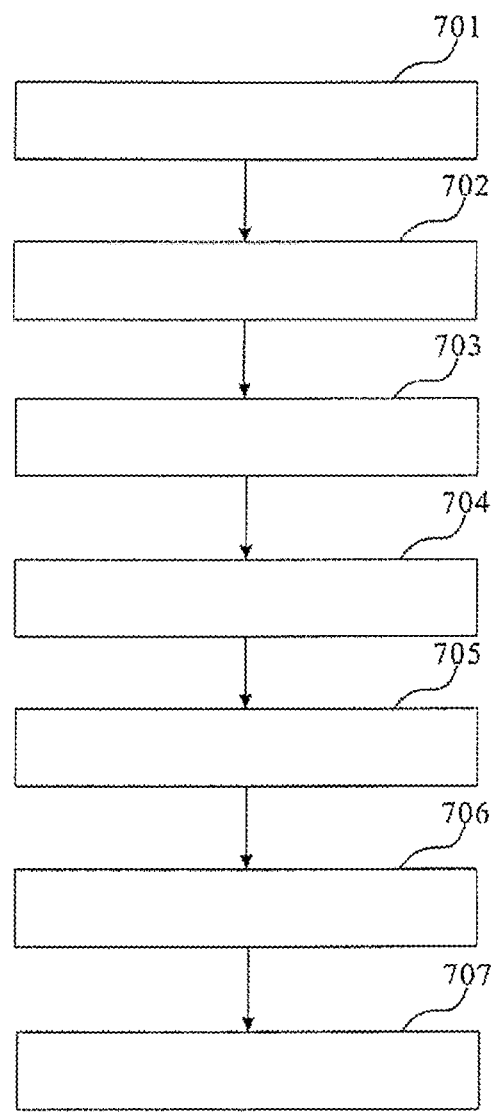
FIG. 6 is a flowchart of another wireless control method in another embodiment of the present invention.

FIG. 6 is an exemplary flowchart of another wireless control method in an embodiment of the present invention. The wireless control method may be applied in a wireless control system comprising a wireless main controller and at least one wireless secondary controller. As FIG. 6 shows, the method may comprise the following steps:

Steps 701-704 are the same as steps 601-604 in FIG. 5, and are not repeated here.

Step 705, the wireless main controller receives an activation request signal entered by a user for a successfully paired wireless secondary controller, and activates communication control with the wireless secondary controller according to an identifier of the wireless secondary controller carried in the activation request signal, then waits to receive a control message from an activated wireless secondary controller, and filters a message of a non-activated wireless secondary controller; and presents activation result information.

Step 706, a wireless secondary controller receives a control signal, carries an identifier of the wireless secondary controller in the control signal, and sends the control signal carrying the identifier to a wireless main controller; the wireless secondary controller is one of the at least one wireless secondary controllers.

In this step, the wireless secondary controller may receive a first sub-signal and a second sub-signal corresponding to the control signal by means of a control button having dual switch contacts; the first sub-signal is a first digital control signal entered via one switch contact of the control button, and the second sub-signal is a second digital control signal obtained by conversion via an analog-to-digital converter of an analog control signal entered via the other switch contact of the control button; the wireless secondary controller compares the first sub-signal and second sub-signal, and if the two are the same, carries an identifier of the wireless secondary controller in the control signal.

Step 707, the wireless main controller receives a control signal from the wireless secondary controller, and determines whether the wireless secondary controller has been paired successfully according to the identifier of the wireless secondary controller carried in the control signal, and if it has been, confirms that the control signal is a valid control signal, and performs corresponding operation control according to the control signal.

In addition, the wireless main controller may furthermore receive a deactivation request signal entered by a user for an activated wireless secondary controller, cancel receipt of a control message from the corresponding wireless secondary controller according to an identifier of a wireless secondary controller carried in the deactivation request signal, and filter a message from the wireless secondary controller; and moreover present deactivation result information.

It can be seen from the solution above that since the CT apparatus in embodiments of the present invention has been provided with a wireless control system comprising a wireless main controller and at least one wireless secondary controller, the wireless main controller receives and identifies a control message from a corresponding wireless secondary controller through a wireless channel, and can realize corresponding operation control, such that the wireless secondary controllers serving as CT apparatus control components can be arranged as required, and no longer be subject to the restrictions of wired connections.

In addition, by performing a paired connection with corresponding wireless secondary controllers one by one, the reliability of data communication with corresponding wireless secondary controllers can be ensured.

Moreover, through the use of verification by comparison of a pairing sequence code and a pairing check code, the reliability of data communication with corresponding wireless secondary controllers can be further ensured.

In addition, by controlling a paired wireless secondary controller to enter an activation state, the operational safety of the CT apparatus can be further ensured.

Furthermore, the provision of independent switch contacts on a control button side of the wireless secondary controller enables the same control signal to be independently sent to a wireless transceiving processor of the wireless secondary controller via channels corresponding to different switch points, so that a single fault of the button can be avoided, thereby further ensuring the operational safety of the CT apparatus.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A wireless main controller for a computed tomography (CT) apparatus, said CT apparatus comprising a plurality of CT apparatus components, said wireless main controller comprising:
   a wireless main control circuit configured to receive a control signal from a wireless secondary controller that carries an identifier of the wireless secondary controller;
   said wireless main control circuit being configured to implement a validity check on the received control signal dependent on said identifier and to emit said control signal from said wireless main control circuit if said control signal passes said validity check; and
   a CT main control circuit configured to receive said control signal from said wireless main control circuit, and to emit at least one control signal to at least one of said CT apparatus components that operates said at least one of said CT apparatus components according to said control signal.

2. A wireless main controller as claimed in claim 1, comprising:
   a human-apparatus interface configured to receive a pairing request signal and to supply the pairing request signal to said CT main control circuit, said pairing request signal also comprising an identifier of a wireless secondary controller;
   said CT main control circuit being configured to supply the pairing request signal to said wireless main control circuit and to thereafter receive pairing result information fed back by said wireless main control circuit, and to present the pairing result information via said human-apparatus interface;
   said wireless main control circuit being configured to send a pairing construction to the wireless secondary controller according to the identifier in the pairing request signal, and to enter into a pairing mode state in which said wireless main control circuit waits to receive a pairing confirmation signal from the identified wireless secondary control signal;
   when a pairing confirmation signal from the identified wireless secondary controller is correctly received by the wireless main control circuit in said pairing mode state, said wireless main control circuit being configured to determine that pairing with the identified wireless secondary controller is successful, and to otherwise determine that pairing with the identified wireless secondary controller has failed;
   said wireless main control circuit being configured to feed back pairing result information to said CT main control circuit and said CT main control circuit being configured, upon determining that pairing with the identified wireless secondary controller is successful, to send pairing result information indicating pairing success to the identified wireless secondary controller; and
   after receiving a control signal from the identified wireless secondary controller, said wireless main control circuit being configured to confirm that the control signal is a valid control signal by determining, based on the identifier of the wireless secondary controller carried in the control signal, that the identified wireless secondary controller has been successfully paired.

3. A wireless main controller as claimed in claim 2, wherein:
   after receiving said pairing request signal, said CT main control circuit is configured to present input prompt information for a pairing sequence code via said human-apparatus interface or via an external display screen, and to carry the pairing sequence code in the pairing sequence request signal and to supply said pairing sequence request signal, with said pairing sequence code therein, to the wireless main control circuit and, upon receiving pairing result information fed back by the wireless main control circuit that indicates successful pairing, to control the human-apparatus interface or the external display screen to stop displaying the input prompt information for the pairing sequence code; and
   said pairing confirmation signal comprising a pairing check code corresponding to the pairing sequence code prompt information, and said wireless main control circuit, after receiving the pairing confirmation signal from the wireless secondary controller, being configured to compare the pairing check code in the pairing confirmation signal with the pairing sequence code carried in the pairing request signal and, when said pairing check code and said pairing sequence code are the same, to determine that the pairing confirmation signal from the wireless secondary controller has been correctly received.

4. A wireless main controller as claimed in claim 2, wherein:
   said CT main control circuit, after receiving the pairing request signal, is configured to carry a pairing sequence code in said pairing request signal, and to supply the pairing request signal carrying the pairing sequence code to the wireless main control circuit; and said wireless main control circuit is configured to carry the pairing sequence code in the pairing instruction and to send said pairing instruction to the corresponding wireless secondary controller and, after receiving a pairing confirmation signal comprising a pairing check code from the wireless secondary controller, to compare the pairing check code in the pairing confirmation signal with the pairing sequence code carried in the pairing request signal and, if said pairing check code in the pairing confirmation signal is the same as the pairing sequence code in the pairing request signal, to determine that the pairing confirmation signal from the wireless secondary controller has been correctly received.

5. A wireless main controller as claimed in claim 2, wherein:
said human-apparatus interface is configured to receive an activation request signal for a successfully paired wireless secondary controller, and to supply the activation request signal to the CT main control circuit, said activation request signal comprising an identifier of a wireless secondary controller;
said CT main control circuit is configured to supply the activation request signal to the wireless main control circuit after receiving the activation request signal, and to receive activation result information fed back by the wireless main control circuit, and to present the activation result information via the human-apparatus interface; and
said wireless main control circuit, after receiving a control signal from a wireless secondary controller, being configured to confirm that the control signal is a valid control signal by determining, based on the identifier of the wireless secondary controller carried in the control signal, that the wireless secondary controller has been paired successfully and activated.

6. A wireless secondary controller, comprising:
a human-apparatus interface;
a wireless transceiving processor;
said human-apparatus interface and said wireless transceiving processor being connected via pins selected from the group consisting of serial peripheral interface pins and input/output pins;
said human-apparatus interface being configured to receive a control signal and to supply the received control signal to the wireless transceiving processor;
said wireless transceiving processor being configured to carry an identifier of the wireless secondary controller in the control signal and to transmit the control signal carrying the identifier;
said human-apparatus interface being configured to receive a pairing confirmation signal before receiving the control signal, and to supply the pairing confirmation signal to the wireless transceiving processor; and
said wireless transceiving processor being configured to receive a pairing instruction from the wireless main controller, and to enter into a pairing mode state, in which said wireless transceiving processor receives the pairing confirmation signal from the human-apparatus interface, and transmits the pairing confirmation signal, and to enter into an operating mode state if a pairing success message is received from the wireless main controller.

7. A wireless secondary controller as claimed in claim 6 wherein said pairing confirmation signal comprises a pairing check code.

8. A wireless secondary controller as claimed in claim 7 wherein said wireless transceiving processor is configured to supply the pairing instruction to the human-apparatus interface, and wherein said human-apparatus interface is configured, at a display screen of the human-apparatus interface, to present the pairing sequence code carried in the pairing instruction.

9. A wireless secondary controller as claimed in claim 6 wherein:
said human-apparatus interface comprises a plurality of control buttons each having an associated first interface circuit, second interface circuit and analog-to-digital converter;
each control button comprising two independent switch contacts, wherein one of said switch contacts is connected to an input/output interface pin of the wireless transceiving processor via the first interface circuit associated with the control button, and the other switch contact is connected to a serial peripheral interface pin of the wireless transceiving processor via the second interface circuit associated with the control button and the analog-to-digital converter associated with the control button; and
the wireless transceiving processor, before carrying the identifier of the wireless secondary controller in the control signal, is configured to compare a control signal received from the input/output interface pin with a control signal received from the serial peripheral interface pin, and if the control signal received via the input/output interface pin is the same as the control signal received via the serial peripheral interface pin, to carry the identifier of the wireless secondary controller in the control signal.

10. A wireless control system for a computed tomography (CT) apparatus, said CT apparatus comprising a plurality of CT apparatus components, said wireless control system comprising:
a wireless main controller and a wireless secondary controller;
said wireless main controller comprising a wireless main control circuit configured to receive a control signal from a wireless secondary controller that carries an identifier of the wireless secondary controller;
said wireless main controller comprising said wireless main control circuit being configured to implement a validity check on the received control signal dependent on said identifier and to emit said control signal from said wireless main control circuit if said control signal passes said validity check;
a CT main control circuit configured to receive said control signal from said wireless main control circuit, and to emit at least one control signal to at least one of said CT apparatus components that operates said at least one of said CT apparatus components according to said control signal;
said wireless secondary controller comprising a human-apparatus interface;
said wireless secondary controller comprising a wireless transceiving processor;
said human-apparatus interface and said wireless transceiving processor being connected via pins selected from the group consisting of serial peripheral interface pins and input/output pins;
said human-apparatus interface being configured to receive a control signal and to supply the received control signal to the wireless transceiving processor; and said wireless transceiving processor being configured to carry an identifier of the wireless secondary controller in the control signal and to transmit the control signal carrying the identifier.

11. A computed tomography (CT) apparatus comprising:
a plurality of CT apparatus components;
a wireless main controller and a wireless secondary controller;
said wireless main controller comprising a wireless main control circuit configured to receive a control signal from a wireless secondary controller that carries an identifier of the wireless secondary controller;
said wireless main controller comprising said wireless main control circuit being configured to implement a validity check on the received control signal dependent on said identifier and to emit said control signal from said wireless main control circuit if said control signal passes said validity check;
a CT main control circuit configured to receive said control signal from said wireless main control circuit, and to emit at least one control signal to at least one of said CT apparatus components that operates said at least one of said CT apparatus components according to said control signal;
said wireless secondary controller comprising a human-apparatus interface;
said wireless secondary controller comprising a wireless transceiving processor;
said human-apparatus interface and said wireless transceiving processor being connected via pins selected from the group consisting of serial peripheral interface pins and input/output pins;
said human-apparatus interface being configured to receive a control signal and to supply the received control signal to the wireless transceiving processor; and
said wireless transceiving processor being configured to carry an identifier of the wireless secondary controller in the control signal and to transmit the control signal carrying the identifier.

\* \* \* \* \*